United States Patent [19]

Cullis et al.

[11] 4,146,172

[45] Mar. 27, 1979

[54] CENTRIFUGAL LIQUID PROCESSING SYSTEM

[75] Inventors: Herbert M. Cullis, Silver Spring, Md.; James H. DeVries, McHenry, Ill.

[73] Assignee: Baxter Travenol Laboratories, Inc., Deerfield, Ill.

[21] Appl. No.: 843,296

[22] Filed: Oct. 18, 1977

[51] Int. Cl.$^2$ .............................................. B04B 5/02
[52] U.S. Cl. ................................. 233/26; 128/214 D
[58] Field of Search ........... 233/1 A, 1 R, 1 D, 14 R, 233/14 A, 17, 18, 23 R, 25, 26, 27, 28; 128/214 D, 2 F

[56] References Cited

U.S. PATENT DOCUMENTS

| | | | |
|---|---|---|---|
| 3,211,368 | 10/1965 | Shanley | 233/26 X |
| 3,655,123 | 4/1972 | Judson et al. | 233/28 X |
| 3,672,564 | 6/1972 | Schlutz et al. | 233/26 |
| 3,674,197 | 7/1972 | Mitchell et al. | 233/26 X |
| 3,743,174 | 7/1973 | Drucker | 233/26 |
| 3,830,425 | 8/1974 | Stallmann | 233/26 |
| 4,010,894 | 3/1977 | Kellogg et al. | 233/27 |
| 4,056,224 | 11/1977 | Lolachi | 233/14 R |
| 4,059,108 | 11/1977 | Latham | 128/214 D |

FOREIGN PATENT DOCUMENTS

2058578  5/1971  France ..................................... 233/26

*Primary Examiner*—George H. Krizmanich
*Attorney, Agent, or Firm*—Henry W. Collins; Eugene M. Cummings; Paul C. Flattery

[57] ABSTRACT

An intervivos blood processing system for centrifugally separating red blood cell and platelet components from whole blood includes a separation chamber for separating red blood cell and white blood cell components, and a collection chamber for collecting platelet components. Each chamber is formed with closely-spaced sidewalls defining respective generally flat interior chambers therebetween and is mounted on a rotatably driven carriage substantially tilted from a parallel arrangement with respect to the carriage axis of rotation at a slight angle whereby the red blood cell component is caused to collect in shoulder regions of the separation chamber and the platelet component is caused to collect on the sidewalls of the collection chamber. The processing chambers are preferably each formed from sheets of flexible hemo-compatible plastic sealed about their periphery to define the chambers therebetween, and are received on the carriage between removable carrier plates having recesses which define the shape of the chambers under fluid pressure.

31 Claims, 13 Drawing Figures

CENTRIFUGAL LIQUID PROCESSING SYSTEM

CROSS REFERENCE TO RELATED APPLICATIONS

This application discloses a fluid processing system and individual processing chambers which may be utilized in conjunction with various types of centrifuge apparatus such as disclosed in application Ser. No. 657,187 filed Feb. 11, 1976 in the name of Housang Lolachi entitled "Centrifugal Liquid Processing Apparatus" and in conjunction with various control systems such as those described in co-pending application Ser. No. 843,222 entitled "Method and Apparatus for Processing Blood" filed Oct. 18, 1977 in the names of Herbert Cullis et al and in the co-pending application Ser. No. 843,223 entitled "Monitor and Fluid Circuit Assembly" filed Oct. 18, 1977 in the name of James DeVries, all of said related cases being assigned to the assignee of the present application. The subject matter of these applications is expressly incorporated herein by reference.

BACKGROUND OF THE INVENTION

The present invention is directed generally to the centrifugal treatment of liquids, and more particularly to a structurally and functionally improved system for centrifugally separating liquid into fractions of different densities. The invention has particular application to the separation of components from whole blood and the present disclosure is directed primarily to this application. However, it will be understood that the system of the present invention is applicable to the treatment of other liquids and semi-liquid masses as well.

Intervivos blood processing, wherein whole blood is taken from a live donor, separated within a processing system into its constituent components, and then returned to the donor, has come into increasingly wide use during recent years. In the course of the processing predetermined portions of the separated blood components, which include plasma, red blood cells, white blood cells, and platelets, as well as subdivisions of these general categories, such as lymphocytes, glanulocytes, and reticulocytes, are either retained for storage or transfer to another patient, or are returned to the donor. Intervivos blood processing operations commonly performed in this manner include plateletpheresis, wherein the platelet component is separated; plasmapheresis, wherein the plasma component is separated; and leukopheresis, wherein the white blood cell components is separated.

Systems for carrying out intervivos blood processing typically include a separation chamber within which whole blood from a donor is subjected to a centrifugal force field. Because of differences in densities, the blood components are congregated in zones at different radial distances from the center of rotation of the separation chamber. Collection ports in the chamber remove the components from these zones for storage or recirculation.

One requirement of continuous flow intervivos blood processing systems is that the volume of blood in process within the system be kept as small as possible to minimize blood deprivement from the patient and the possibility of ill effects should operation of the apparatus be inadvertently interrupted. Furthermore, it is necessary that the flow defining portions of the system be sterile and disposable to minimize the possibility of contamination, and that the system and its associated centrifugation apparatus be simple to operate, and not require constant operator supervision. Certain prior art systems utilized processing chambers in the form of specially shaped bowls which required expensive manufacturing techniques and could not be formed by high volume production techniques. The system of the present invention provides a lower in-process volume than prior art sytems, and readily lends itself to automation to reduce operator requirements.

Another requirement of intervivos blood processing systems is that the processing operation be carried out as efficiently as possible at the highest possible flow rate to avoid unnecessary inconvenience to the patient. Previously, collection of ten standard units of platelets as defined by the Bureau of Biologics, U.S. Food and Drug Administration, required from 2 ½ to 4 hours, whereas in the system of the present invention less than 1 ½ hours are typically required to collect the same quantity of platelets.

Furthermore, the components separated by the processing system must be consistently high purity. In prior art systems the separated blood components were subject to intermixing, partially as a result of coriolis currents induced by rotation of the processing chamber, and partially as a result of inherent inefficiency in the separation process. The result of this intermixing was that a portion of the separated components had to be discarded, which had the effect of lowering the yield of the system. Typically, in prior art plateletpheresis applications a white blood cell component of from 15 to 20 percent was present in the derived platelet component. The present system provides a substantial improvement in the purity of the platelet component, typically providing a white blood cell component of less than 2 percent in the collected platelet component.

SUMMARY OF THE INVENTION

The invention is directed to an intervivos blood processing system and the processing chambers provided therein for centrifugally separating red blood cell and platelet components from whole blood. The system comprises a thin processing chamber having first and second closely spaced sidewalls defining an interior chamber including at least one collection region, outlet means for withdrawing fluid from the collection region of the chamber, and means including inlet means and an additional outlet means defining a flow path for delivering blood to be processed to the chamber. Means including a rotatably driven carriage are procided for rotating the chamber with the chamber mounted generally perpendicular to a radius of the rotor whereby the red blood cell component is caused to collect in the collection region of the chamber.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENTS

Figure 1:
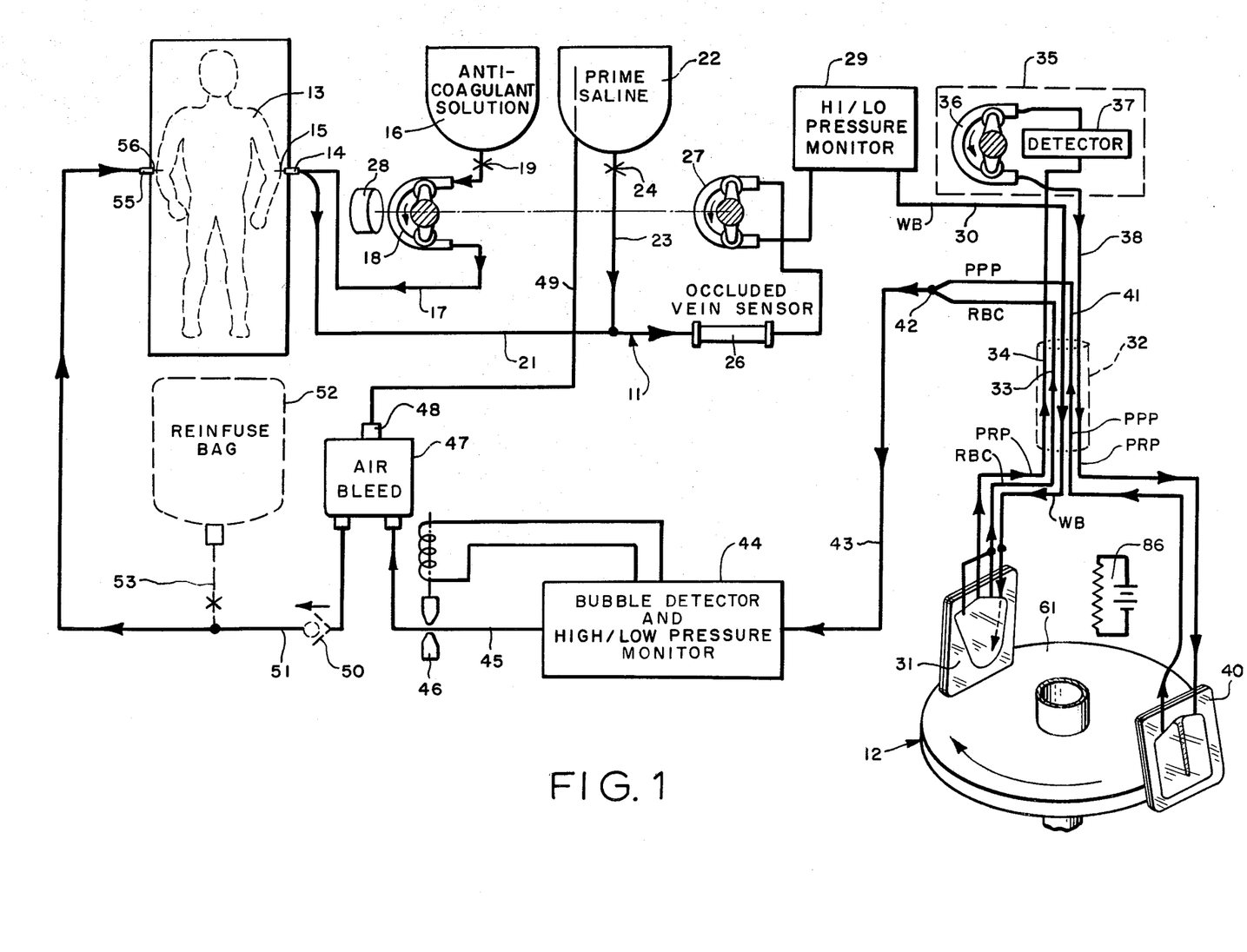
FIG. 1 is a functional diagrma, partially in block form, illustrating an intervivos blood processing system constructed in accordance with the invention.

Referring to the Figures, and particularly to FIG. 1, a processing system for accomplishing platelet-pheresis in accordance with the invention is seen to consist of a disposable flow system, generally indicated as 11, formed of polyvinylchloride (PVC) or other suitable hemo-compatible plastic material. The processing system is shown in conjunction with a donor 13, from whom blood is being taken, processed and returned, and in conjunction with a centrifugation apparatus 12 wherein portions of the flow system are subjected to a centrifugal force field during processing of the blood.

The flow system 11 includes a needle adapter 14 fitted with an appropriate needle 15 through which whole blood is removed from the donor. An anticoagulant solution such as ACid Citrate Dextrose (ACD) or heparin is injected from a container 16 into the flow of whole blood at needle adapter 14 by means of a tubing segment 17 and a peristaltic pump 18 of conventional design and construction. A manually operated tubing clamp 19 upline of the peristaltic pump 18 permits replacement of container 16 with a full container as the anticoagulant solution is depleted. During blood processing pump 18 operates at a steady controlled rate commensurate with the flow rate of the whole blood through the system so as to cause a metered amount of the anticoagulant solution to be added to the whole blood as it is removed from the patient.

To facilitate purging air from flow system 11 prior to initiating blood flow provision is made for priming the system with a saline solution from a container 22. The container is connected to tubing segment 21 by a tubing segment 23 and operator-actuable valving means 24. Prior to introducing blood into the system solution from container 22 is caused to flow through the system to displace air from the system.

Whole blood with anticoagulant solution added next flow through an occluded vein sensor 26 which continuously monitors fluid flow through the system. Upon interruption or restriction of flow, such as may occur as a result of a collapsed vein, a blood clot, or kinked tubing, sensor 26 interrupts operation of the system and sounds an alarm to alert medical personnel to the interruption. The occluded vein sensor 26 may be conventional in construction and operation, consisting for example of a section of silastic tubing the diameter of which is monitored by means of a microswitch or similar electrical sensor. In the event of flow restriction, the tubing section is deflected by pressures within the system and the resulting control effect generated by the sensor is utilized by appropriate control circuitry (not shown) to interrupt operation of the system and sound the alarm. Other types of occluded vein sensors capable of providing the same protection may be utilized where appropriate.

The whole blood and anticoagulant solution passing through sensor 26 next passes through a second peristaltic pump 27 which establishes a precisely metered flow rate through the system. Peristaltic pump 27 is preferably integral with or otherwise synchronized to peristaltic pump 18 so that the quantity of anticoagulant solution added from reservoir 16 remains at a constant ratio to the flow rate established within the system by pump 27. To this end, the two peristaltic pumps 18 and 27 may be driven by a single motor 28.

Downline of peristaltic pump 27 the whole blood flows through a high-low pressure monitor 29 which interrupts system operation when system pressure falls outside of a predetermined operating range. From monitor 29 the blood flows through a tubing segment 30 to a red blood cell separation chamber 31, which is mounted to the rotor of centrifugal apparatus 12 and is subjected to a centrifugal force field during operation of the system. To facilitate fluid communication between the rotating chamber 31 and the stationary portions of the system, a portion of tubing segment 30 may comprise one of several passageways within a multiple-passageway umbilical cable 32 extending between the rotating and stationary portions of the system. As will be seen presently, this umbilical cable is conveyed by apparatus 12 so as to maintain seal-less fluid communication without becoming twisted.

The function of the red blood cell separation chamber 31 is to separate the red blood cell (RBC) and white blood cell (WBC) components from the whole blood. Since the major portion of the separated product is RBC component, the combined RBC and WBC separation product will hereafter be referred to as the RBC component. The separated RBC component flows from the chamber through a conduit segment 33, which comprises another passageway in umbilical cable 32. The remaining blood and anticoagulant solution, which comprises a platelet rich plasma (PRP) component, flows from separation chamber 31 through a conduit segment 34 to a variable-rate pump assembly 35.

The function of pump assembly 35, which is described in the co-pending application entitled "Method and Apparatus for Processing Blood", Ser. No. 843,222, filed concurrently herewith, is to pump the PRP component from chamber 31 at a rate commensurate with the rate of red blood cell separation so that separation of the PRP and RBC components continues within the chamber. Basically, this is accomplished within pump assembly 35 by means of a peristaltic pump 36 and associated RBC component detector 37. As will be described in greater detail later, the pump is periodically cycled to remove first PRP component, and then RBC component, from the chamber. Upon detection of the RBC component by detector 37 pump 36 is stopped and momentarily reversed to return the RBC component to the chamber and reestablish the separation process within the chamber.

Downline of pump assembly 35 the PRP component is conveyed through a tubing segment 38, a portion of which comprises another passageway in umbilical cable 32, to a platelet collection chamber 40. In chamber 40 platelets are removed from the PRP component, leaving a solution of platelet poor plasma (PPP) to be conveyed through a tubing segment 41 to a Y connection 42 wherein the PPP component is combined with the RBC component separated in chamber 31. The resultant fluid, which essentially comprises platelet poor whole blood, flows through a tubing segment 43 to a bubble detector and high-low pressure monitor 44. The purpose of monitor 44, which may be conventional in construction and operation, is to continuously monitor the platelet poor whole blood in tubing segment 44 for the presence of bubbles or inappropriate or out-of-range pressure, and upon the occurrence of either of these conditions to generate a control effect for terminating the blood processing operation and sounding an alarm. Downline of monitor 44 the platelet poor whole blood flows through a tubing segment 45 to an electrically-controlled valve 46 which blocks flow through the system by occluding the tubing segment upon occurrence of a bubble or loss of pressure. The blood next passes through an air bleed expansion chamber 47, which includes an air bleed valve 48 for returning air formed within the system to container 22 through a tubing segment 49. A tubing segment 51 connects the air bleed chamber 47 to the donor.

An optional reinfuse bag or container 52 may be connected by a tubing segment 53 to tubing segment 51 to reduce flow variations in the platelet poor whole blood being returned to the donor. In the event this container is provided, a check valve 50 may be provided in tubing segment 51 to preclude the possibility of reverse flow from the donor. Tubing segment 51 connects with a second needle adapter 55, which is fitted with a needle 56 to effect return of the platelet poor blood to the donor.

Figure 2:
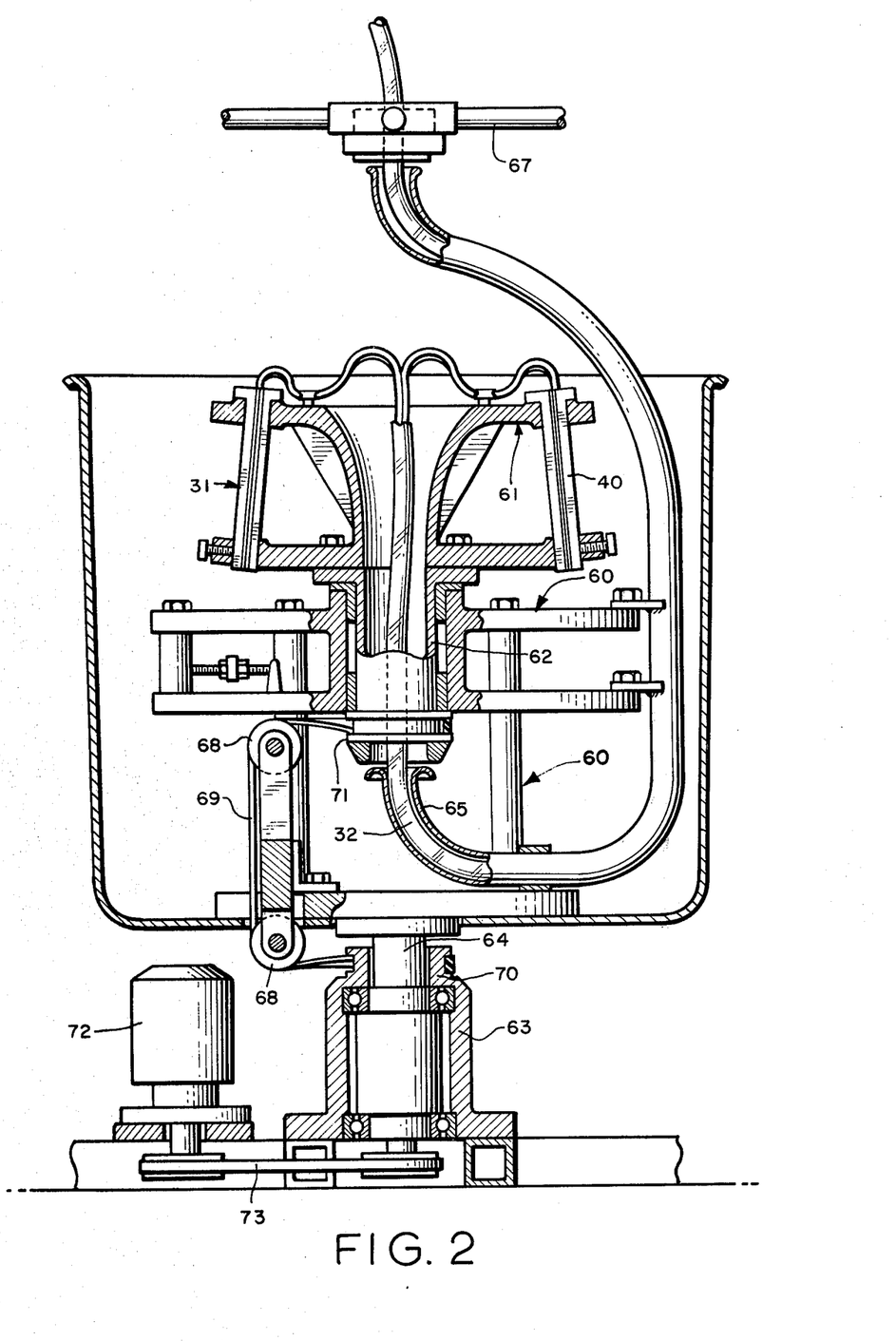
FIG. 2 is a front elevational view partially in cross-section of a preferred form of centrifuge apparatus for use in conjunction with the blood processing system of FIG. 1.

Referring to FIG. 2, the liquid processing system 11 of the invention may be utilized in conjunction with a seal-less centrifugation apparatus such as that described and claimed in the co-pending application of Houshang Lolachi, Ser. No. 756,187, filed Feb. 11, 1976, and assigned to the present assignee. Basically, this centrifugation apparatus includes a rotor drive assembly 60 to which a rotor assembly or carriage 61 is journaled by means of a hollow support shaft 62. The rotor drive assembly 60 is itself journaled to a stationary hub assembly 63 by means of a vertical drive shaft 64. A guide sleeve 65 is mounted on the rotor drive assembly.

The red blood cell separation chamber 31 and the platelet collection chamber 40 of the processing system are seated on the rotor assembly 61. Fluid communication is established between the two chambers, which rotate with the rotor assembly, and the non-rotating portions of the processing system, by means of the five channel umbilical cable 32 which is seen to extend from a central location along the axis of rotation of the rotor downwardly through the center of the drive shaft 62, radially outwardly through guide sleeve 65, and upwardly to a fixed axially aligned position established by a support arm 67. As described in the previously identified co-pending application Ser. No. 675,187, the routing of the umbilical cable 32, together with the rotor assembly 61 and rotor drive assembly 60 being driven in the same direction with a speed ratio of 2:1, establishes fluid communication with chambers 31 and 40 without the cable becoming twisted. Instead, the umbilical cable is subjected only to flexing, or repeated partial twists about its axis through angles not in excess of 180 degrees, as the rotor assembly 61 rotates.

A 2:1 speed ratio is obtained between the rotor and rotor drive assembly by means of two pairs of idler pulleys 68 mounted on rotor drive assembly 60 and a drive belt 69. The drive belt is routed over these pulleys and into engagement with a stationary ring-type pulley 70 mounted on hub 63 at one end, and a rotor drive pulley 71 carried on the bottom end of the rotor drive shaft 62 at its other end. As the rotor drive assembly 60 is rotated clockwise by means of a motor 72 and drive belt 73 driving drive shaft 64, drive belt 69 establishes a clockwise rotation of rotor assembly 61. Assuming that stationary pulley 70 and rotor drive pulley 71 have the same diameter, the rotational speed of rotor assembly 61 will be exactly twice that of rotor 60 by reason of the combined effect of the direct 1:1 drive relationship of pulleys 70 and 71 and the planetary motion of pulleys 68 about the axis of rotation of rotor drive assembly 61.

The blood processing system of the invention is preferably manufactured as a single disposable unit in which umbilical cable 32 is included. To install this system in the apparatus the free end of the umbilical cable may be threaded downwardly from support arm 67 through the hollow support sleeve 65 and then upwardly through the hollow rotor support shaft 62. The other end of the cable is then connected to the other components of the system. Since the system remains sealed when installed, all possibility of compromising the sterility of the system is avoided. After use, the entire flow system may be removed from the apparatus and disposed of.

Figures 3, 4, 5:
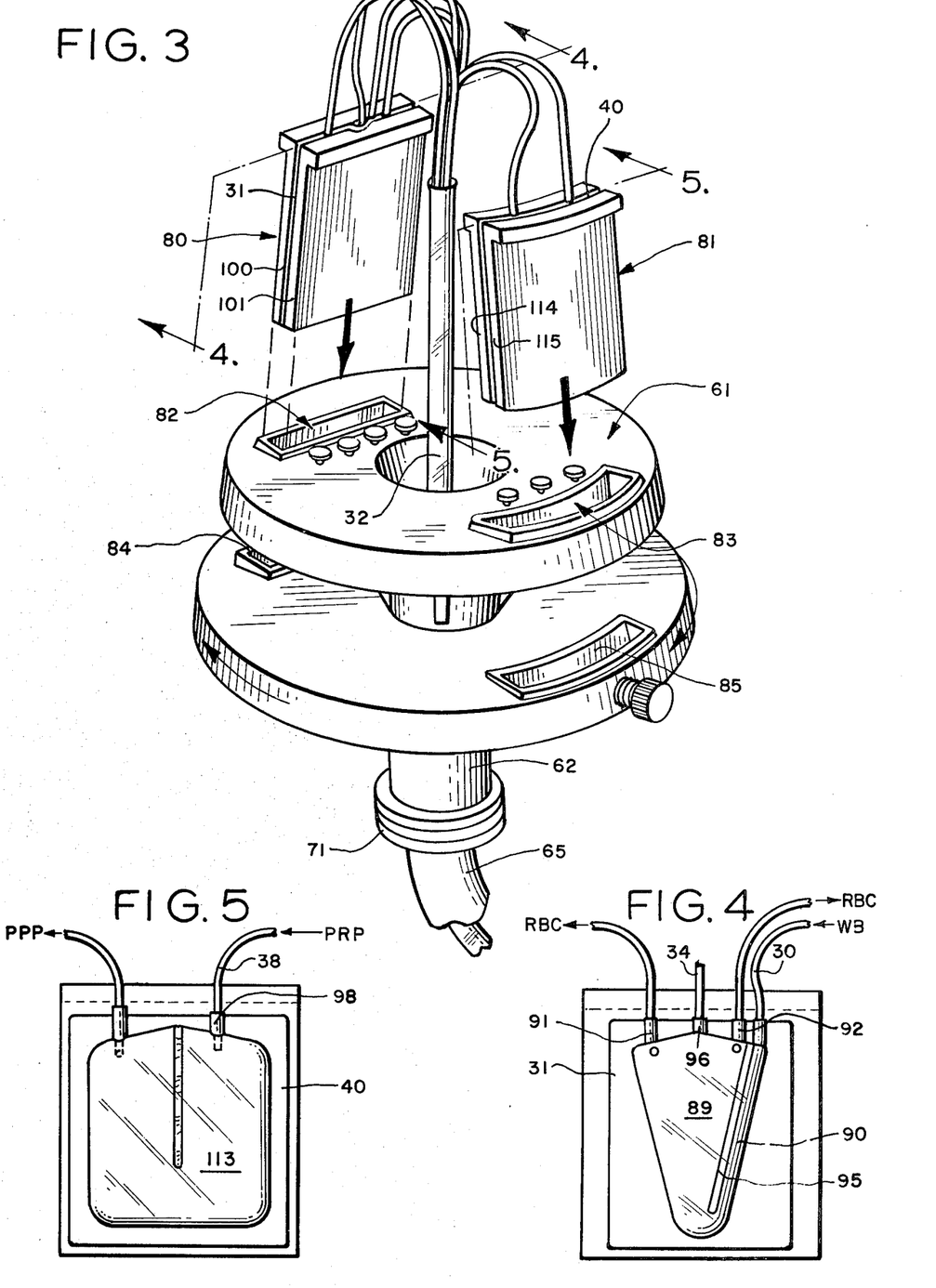
FIG. 3 is an enlarged perspective view of the rotor portion of the processing apparatus of FIG. 2 showing the processing chambers of the processing system prior to insertion in the rotor.
FIG. 4 is a front elevational view of the red blood cell separation chamber and associated carrier of the blood processing system.
FIG. 5 is a front elevational view of the platelet collection chamber and associated carrier of the blood processing system.

Referring to FIG. 3, in accordance with one aspect of the invention, installation and removal of blood processing chambers 31 and 40 from the carriage 61 of the centrifuge apparatus is facilitated by providing respective carrier assemblies 80 and 81 respectively for the chambers. These carriers, which each comprise a pair of generally rectangular plates between which the chambers are sandwiched, are slidably received in respective sockets 82–85 provided on rotor assembly 61. The sockets may be arranged in pairs on top and bottom parallel-spaced horizontal rotor plates as shown, or may be formed as part of a solid rotor core. In either case, it is desirable that the sockets and carrier plates be formed of a material of high thermal conductivity, such as aluminum, so that the temperature of the blood passing through the chambers can be more readily controlled. To this end a resistance heating element 86 (FIG. 1) or other active thermal element such as a hot air blower, may be provided in thermal communication with the rotor to heat the carrier plates to a desired temperature, typically body temperature or 37° C., during processing. This provides for more consistent and efficient sedimentation, and reduces the possibility of thermal shock as the processed blood is reintroduced into the donor.

Referring to FIGS. 4 and 6-8, the red blood cell separation chamber 31 is seen to consist of two sheets 87a and 87b of polyvinylchloride or other hemo-compatible plastic material bonded or otherwise joined together along a seam 108 to form therebetween a compartment 89 having a relatively narrow rounded lower portion and a relatively wide upper portion. Whole blood to be processed from tubing segment 30 is admitted to this compartment at the lower portion thereof (as viewed in FIG. 4) through a passageway 90, which may be formed by providing an interior wall 95 (FIG. 4) along one side of the compartment, either by compressing sheets 87a and 87b together by means of ribs 93a and 93b (FIG. 7) on the inside surfaces of the carrier plates, as shown, or by providing a heat seal or bond between the sheets. Alternatively, the passageway can be established by means of a tubing segment within the chamber extending from tubing segment 30.

Figure 8:
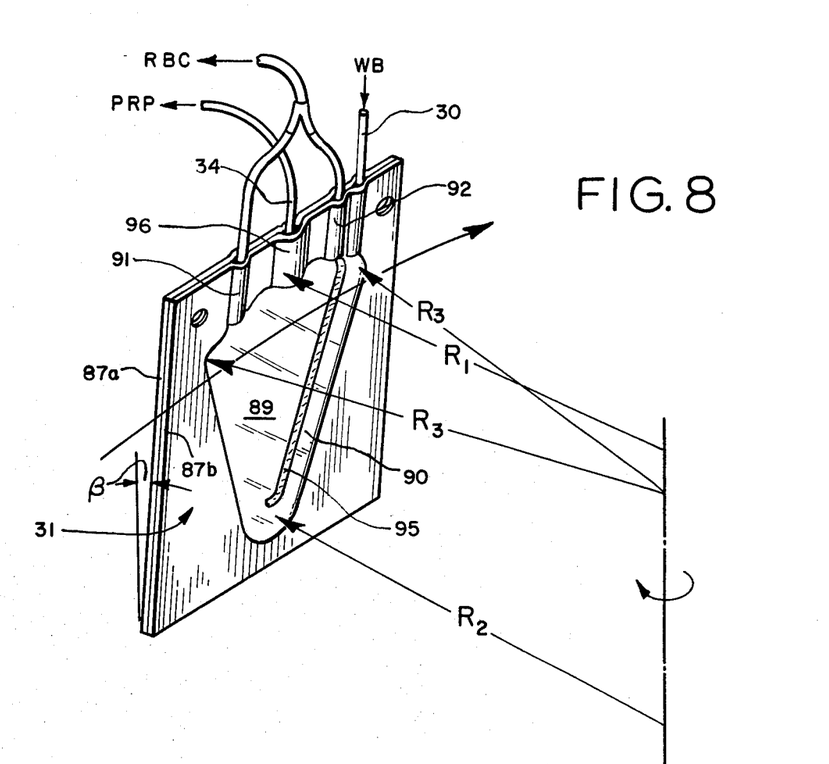
FIG. 8 is an enlarged perspective view of the red blood cell separation chamber showing the associated radii thereof.

Under the influence of a centrifugal force field, whole blood within the chamber is caused to separate, with the heavier RBC and WBC components collecting at collection regions within the chamber corresponding to the locations of greatest radial extent from the axis of rotation of the carriage, in this case the upper left and right corners or shoulders of the chamber as may be seen in FIG. 8 at $R_3$. The less dense platelet rich plasma component remains primarily outside of the collection regions, in this case within a region extending downwardly from the top margin of the chamber between the shoulder regions.

The separated RBC component is removed from chamber 31 through two collection ports 91 and 92 along the top margin thereof which communicate with the collection regions of the chamber. These collection ports are connected by respective short tubing segments to a Y coupling (FIG. 8) and by this coupling to tubing segment 33. An additional port 96, centered between ports 91 and 92 and slightly offset with respect to the top margin of the chamber, removes the PRP component from the chamber through tubing segment 34.

Although the collection regions in which the red blood component collects in the present embodiment are located at the two upper corners or shoulders of the separation chamber by reason of the configuration of the chamber, it will be appreciated that the collection regions may have different locations in other chamber configurations. For example, with a generally rectangular chamber mounted in a plane generally perpendicularly to a radius of the carriage and having no incline with respect to the axis of rotation, the collection regions would be located along the two vertical margins of the chamber since these regions would be at the largest cylindrical radius from the axis of rotation.

Referring to FIGS. 5 and 11-13, the platelet collection chamber 40 is constructed of two sheets 97a and 97b of hemo-compatible plastic material, bonded together to form an interior compartment 94 of generally rectangular configuration. An inlet port 98 provided adjacent one upper corner of the chamber admits PRP component to the chamber from conduit segment 38, and an outlet port 99 adjacent the other upper corner allows PPP component to be withdrawn from the chamber through tubing segment 41. An interior wall 88 (FIG. 12) within chamber 40, which may be formed either by a bond between the sheets, or by compression of the sheets by means of appropriately positioned ribs on the chamber carrier plates, defines a circuitous flow path within the chamber between ports 98 and 99. The effect of this is to increase the effective length of the flow path, thereby increasing the collection efficiency of the chamber.

Figure 6:
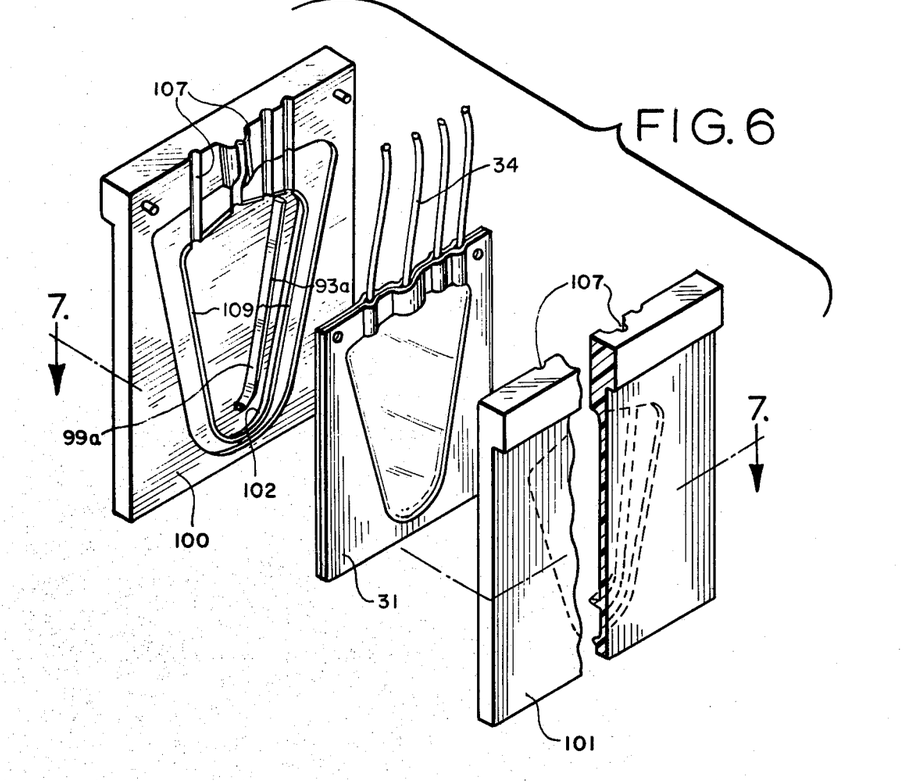
FIG. 6 is an enlarged exploded perspective view of the red blood cell separation chamber and its carrier.
Figure 7:
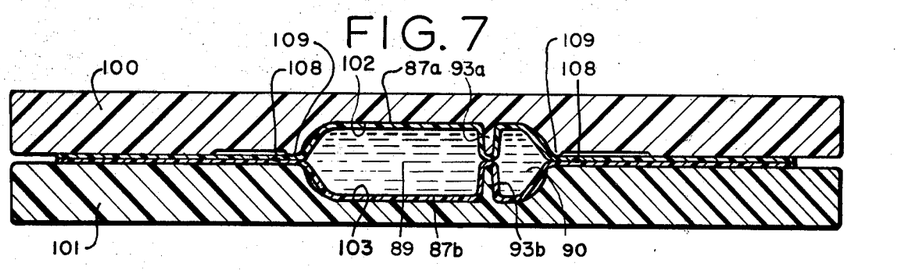
FIG. 7 is a cross-sectional view of the red blood cell separation chamber and carrier in an assembled state taken along line 7—7 of FIG. 6.

Referring to FIGS. 6 and 7, the separation chamber carrier assembly 80 comprises a pair of rectangular plates 100 and 101 formed of metal or other material having a high degree of thermal conductivity. Plates 100 and 101 include recesses 102 and 103 on their inside surfaces which form compartments for receiving separation chamber 31 when the plates are joined together. A plurality of channels 107 on the inside surfaces of the plates provide passageways for the conduit segments associated with the separation chamber.

When separation chamber 31 is filled with blood sheets 97a and 97b expand into recesses 102 and 103 such that the ultimate dimensions of the chamber are established by the recesses. Pressure on seam 108 (FIG. 7) is relieved at this time by providing an interior rib 109 on plate 100 around the periphery of recess 102. The effect of this rib is to compress sheets 87a and 87b at the margins of recesses 102 and 103, thereby accurately defining the margin of separation between chamber 89 and inside seam 108, notwithstanding dimensional errors in the seam as a result of autoclaving of manufacturing operations.

Figure 9:
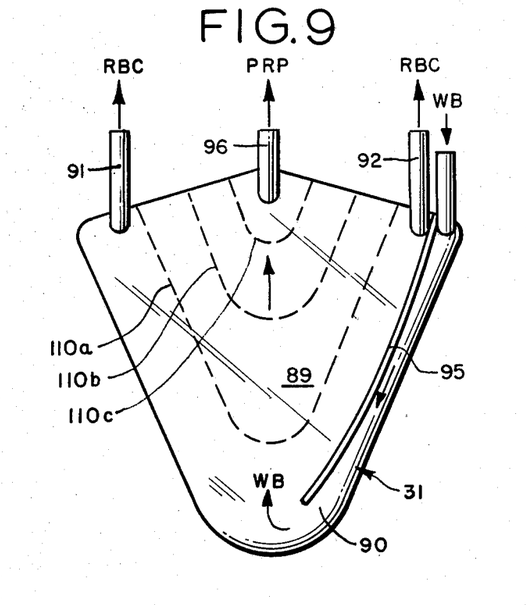
FIG. 9 is a diagrammatic front elevational view of the red blood cell separation chamber illustrating the operation thereof.

When seated in sockets 82 and 84, separation chamber 31 is aligned with its largest dimensions in a plane generally tangent to the surface of the right circular cone oriented with vertex upward having an axis of symmetry colinear with the axis of rotation and generated by an angle of magnitude $\beta$. Thus the substantially planar configuration of separation chamber 31 appears to be tilted at an angle $\beta$ with respect to the axis of rotation of the rotor. This results in the shoulder-located collection regions of the chamber being positioned at a cylindrical radius $R_3$ with respect to the axis of rotation which is greater than the cylindrical radius $R_1$ of the PRP collection port 96, and the cylindrical radius $R_2$ of the lower portion of the chamber. As a result, under centrifugation the heavier RBC component in the whole blood collects at the shoulders of the chamber as whole blood is pumped in through passageway 90. With time the RBC component migrates to and congregates in a region which extends from the shoulders of the chamber and along the sides of the chamber, forming boundary 110a (FIG. 9) between the RBC and PRP component. The RBC component is withdrawn through ports 91 and 92, while the remaining relatively lighter PRP component is withdrawn through port 96.

By reason of the boundary 110 closely approximating the profile of the chamber walls, maximum interface area is achieved between the PRP and RBC components for maximum separation efficiency. In practice, this is established primarily by the tilt angle $\beta$, which is set to establish the boundary generally parallel to the sidewalls of the chamber. In one successful embodiment of the invention, an angle $\beta$ of approximately 1 degree provided good results with a chamber 3 inches wide and 5.5 inches high mounted at a radius of 10 cm.

Operation of pump assembly 35 results in the PRP component accumulated in the region of port 96 being removed from the chamber, with the result that the PRP collection region progressively decreases as shown by contours 110a–110c. Eventually, given a pumping rate greater than the separation rate of the PRP component, the PRP component is exhausted and the RBC component is removed through port 96. As previously developed, when this component is detected by detector 37, the pump is reversed for a sufficient period of time to return the RBC component to the chamber and reestablish the separation process.

Collection port 96 may be offset to a lesser radius than ports 91 and 92 to improve separation efficiency by allowing a greater percentage of the PRP component to be withdrawn prior to the RBC component being withdrawn. This results because the RBC component tends to collect along the rear wall of the chamber because of its greater density.

Figure 10:
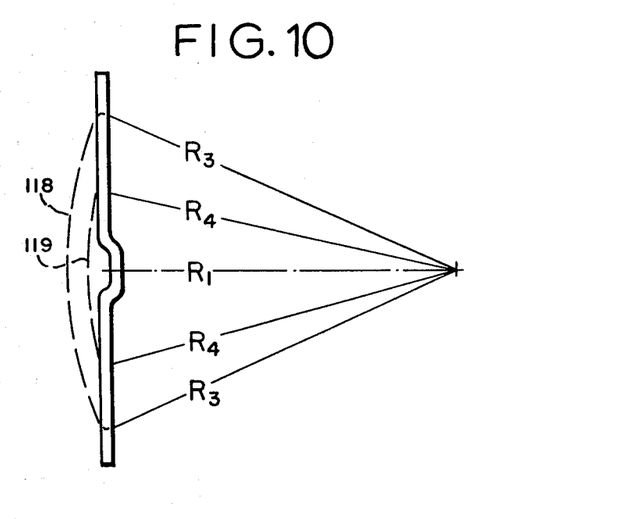
FIG. 10 is a diagrammatic top plan view showing the radii of the red blood cell separation chamber.

The flat cross-section and tangential orientation of separation chamber 31 works to minimize the effects of coriolis forces within the chamber. As illustrated in FIG. 10, the progressively decreasing radius of the chamber between the shoulders and the center of the chamber resists circulation of fluid brought about by rotation of the chamber. This is illustrated by the fact that the arc 118 and 119 of radius $R_3$ and an intermediate radius $R_4$ extend outside of the chamber walls. Thus, the radial path required for coriolis circulation with the chamber does not exist, and as a result minimum mixing occurs between the sedimented RBC component and the PRP component.

An additional requirement for optimum yield and purity is that the sedimentation rate and residence time within the separation chamber be carefully controlled. Since the rate of sedimentation is a function of the magnitude of the centrifugal force field, and the total quantity of RBC component sedimented for a chamber of given volume is dependent on the residence time of the blood in the force field, it is necessary that both flow rate and rotational speed be controlled if optimum results are to be obtained. In one successful embodiment of the invention, for a chamber 3 inches wide and 5.5 inches high of 45 ml. volume, and a rotor speed of 1400 RPM and a radius $R_1$ of approximately 10 cm, liquid passing through the chamber is subjected to a centrifugal force of approximately 220 G's. For a flow rate of 33 ml. per minute, a yield of approximately 18 ml. of PRP per minute is realized under optimum conditions for typical blood having a hemocrit of 42.

Figure 11:
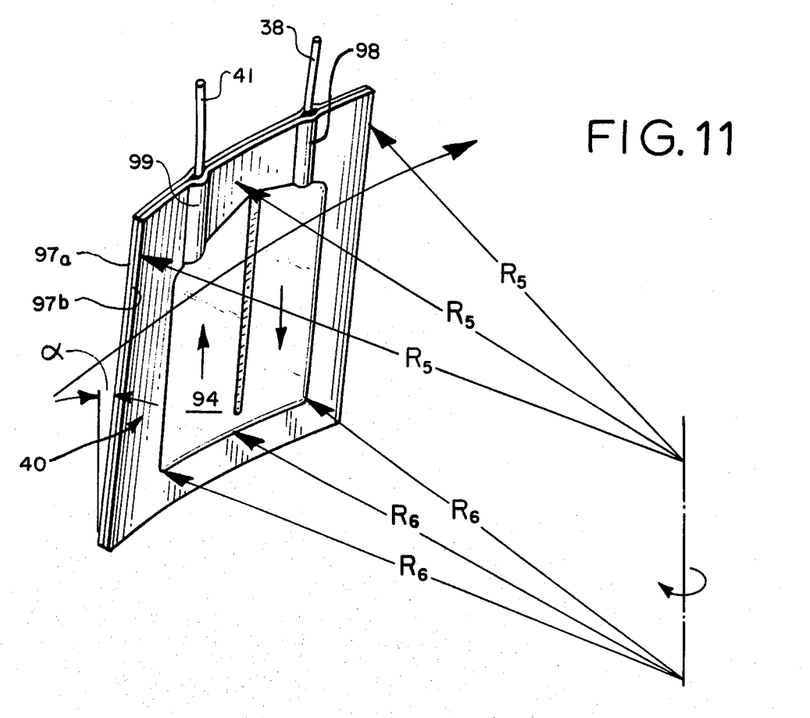
FIG. 11 is an enlarged perspective view of the platelet collection chamber showing the associated radii thereof.
Figure 12:
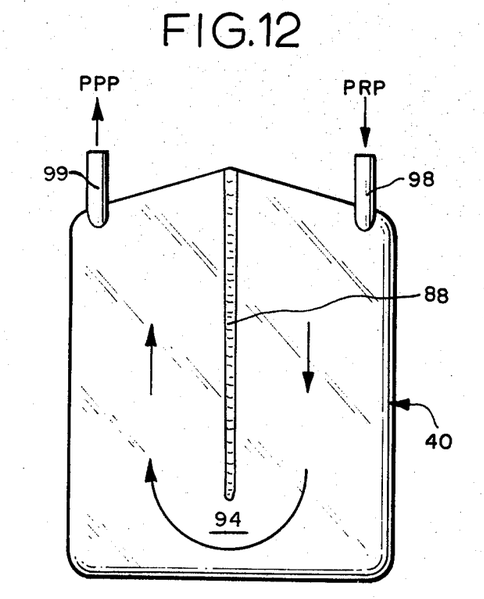
FIG. 12 is a diagrammatic front elevational view of the platelet collection chamber illustrating the operation thereof.
Figure 13:
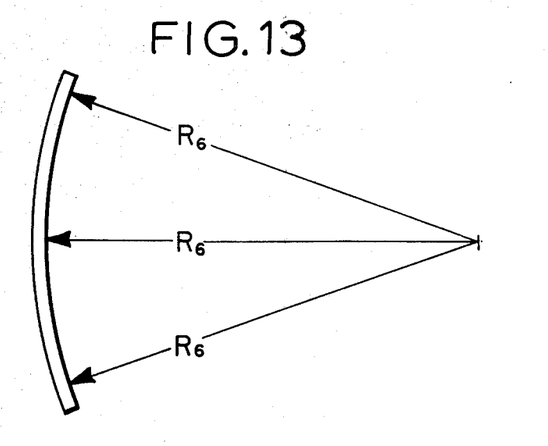
FIG. 13 is a diagrammatic top plan view showing the radii of the platelet collection chamber.

As seen in FIG. 11, the platelet separation chamber 40 may be arcuate in cross-section, having a constant radius $R_6$ with respect to the axis of rotation of the rotor. With this arrangement, the PRP component is subjected to a substantially uniform centrifugal force field as it flows from port 98 to port 99. As a result, sedimentation takes place evenly along the circuitous flow path defined within the chamber, the platelets being evenly deposited on the chamber walls.

As may be seen in FIG. 3, the collection chamber carrier 81 comprises two arcuate plates 114 and 115 adapted to seat within sockets 83 and 85 on carriage 61. Chamber 40 is received within a compartment formed between the plates by recesses in the plates. The upper margin of chamber 40 may be inclined at an angle α (FIG. 11) toward the axis of rotation of the carriage to provide a radius $R_6$ at the bottom of the chamber greater than the radius $R_5$ at the top. Thus the shape of collection chamber 81 in its largest dimensions corresponds to a region on the surface of a frustrum of a right circular cone oriented with vertex upward, having an axis of symmetry colinear with the axis of rotation of rotor 61 and generated by an angle of magnitude. This has the effect of forcing bubbles trapped within the chamber to the top of the chamber where they can be more easily purged from the system.

To obtain efficient sedimentation of the red blood cell component in separation chamber 31 it is desirable that a relatively high flow velocity be maintained through the chamber and to this end the interior volume of the chamber is preferably relatively small, typically 45 ml. With high flow velocities the relatively light platelets are not subjected to the centrifugal force field for a sufficient period of time to allow appreciable sedimentation, and as a result practically all of the platelets are carried from chamber 31 with the plasma component. It is this PRP component which is pumped into the platelet collection bag 40 by pump assembly 35. Because of the need for a higher flow rate in the red blood cell separation chamber a higher centrifugal force field may be desirable for this chamber than that required for the platelet collection chamber. Accordingly, the red blood cell separation chamber may be placed at a greater radius from the axis of rotation than the platelet collection chamber, resulting for example in a force field of approximately 280 G's at the red blood cell separation chamber compared with a force field of approximately 220 G's at the platelet collection chamber in the illustrated embodiment.

It is desirable to have relatively low flow velocity in platelet collection chamber 40 to allow the relatively low mass platelets more time to sediment under the influence of the centrifugal force field. To this end, the platelet collection chamber is preferably constructed with a larger volume than the red blood cell separation chamber so that a lower flow velocity results through the bag. The lower flow velocity reduces the possibility of potentially damaging shear forces from developing between the platelets as they sediment. Typically, the platelet collection bag may have a volume of approximately 160 ml., which provides a low flow velocity without unduly compromising the overall object of the system that in-process volume be minimized.

In practice, with the 45 ml. red blood cell separation chamber and the 160 ml. platelet collection chamber, a total system volume of approximately 300 ml. was realized. This is well within the 600 ml. design criteria established by the Bureau of Biologics, U.S. Food and Drug Administration, as constituting a maximum unit of blood to be removed from the human body at one time.

The entire flow system, including the red blood cell separation chamber and the platelet collection chamber, is preferably constructed as a sealed pre-sterilized system which can be disposed of after use. It is contemplated that the platelet collection bag 40 will be severed from the connecting tubing segments 38 and 41 after use to facilitate removal of the collected platelets. Also, it is contemplated that the ACD and prime solutions may be supplied in separate sterile containers prior to use without compromise to the sterility of the system.

Although the invention has been shown in conjunction with a plateletpheresis system, it will be appreciated that the principles of the invention can be practiced in performing other operations, including plasmapheresis wherein the platelet poor plasma component is not recombined with the red blood cell component, but is instead directed to a reservoir for storage, or immediately infused in another donor.

Although the processing chambers have been shown in the form of plastic bags formed by a seal between two sheets of plastic, it will be appreciated that the chambers can be formed by other methods, such as by blow molding. Furthermore, where advantageous, the chambers can also be formed with rigid walls, thereby obviating the need for carriers 80 and 81.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A blood processing system for centrifugally separating the red blood cell component from whole blood comprising, in combination:
    a thin processing chamber having first and second closely spaced sidewalls defining an interior chamber having a collection region therein;
    inlet means included in said chamber for admitting blood thereto;
    outlet means for withdrawing fluid from said collection region;
    means defining a flow path for delivering blood to be processed to said inlet means; and
    means including a rotatably driven carriage for rotating said chamber, said chamber being mounted generally in a plane which is inclined from parallel with the axis of rotation of said carriage to have a smaller cylindrical radius from the axis of rotation of said carriage at one end thereof than at the other end thereof to increase the tendency of the red blood cell component to collect in said collection region.

2. A blood processing system as defined in claim 1 wherein the largest dimensions of said chamber lie in a plane transverse to a line along the direction of said thin dimension and said one end of said chamber is relatively wide to include said collection region and said other end of said chamber is relatively narrow and of rounded shape.

3. A blood processing system as defined in claim 2 wherein said outlet means comprise an outlet port adjacent said collection region at said one end of said chamber.

4. A blood processing system as defined in claim 3 wherein said inlet means is disposed adjacent said other end of said chamber.

5. A blood processing system as defined in claim 1 wherein said processing chamber is distensible and formed in a collapsed flat condition, and wherein said carriage includes a carrier comprising first and second rigid plates defining therebetween an interior compartment for receiving said processing chamber and removable from said rotor to facilitate loading said chamber therein, whereby when the interior of said chamber is filled with blood to be processed said chamber assumes the predetermined configuration of said interior compartment.

6. A blood processing system as defined in claim 5 wherein said processing chamber is formed from first and second sheets of hemo-compatible plastic with a peripheral seal therebetween.

7. A blood processing system as defined in claim 6 wherein said carrier contains rib or ridge means establishing a pressure seal inwardly of said peripheral seal with respect to said chamber to relieve the pressure that would otherwise be exerted by the contents of said chamber on said peripheral seal.

8. A blood processing system as defined in claim 1 wherein said processing chamber is distensible and formed in collapsed flat condition from first and second sheets of hemo-compatible plastic with a peripheral seal therebetween.

9. A blood processing system as defined in claim 1 wherein collection means are provided for deriving blood to be processed from a donor, and injection means are provided for returning processed blood fluid to the donor.

10. A blood processing system as defined in claim 1 including additional collection means for deriving the platelet component from whole blood, and means for establishing fluid communication between said interior chamber and said additional collection means.

11. A blood processing system as defined in claim 10 wherein said additional collection means comprise a second chamber having closely spaced generally cylindrical sidewalls defining a thin interior chamber therebetween, said second chamber including an inlet port and an outlet port, and wherein flow defining means are provided between said second chamber and said first processing chamber to permit plasma from said second chamber to be combined with said red blood cell component from said first chamber, and wherein said second chamber is mounted for rotation on said rotor and aligned with said thin interior chamber thereof substantially symmetric about the axis of rotation of said rotor whereby platelets are collected on the internal surfaces of said sidewalls during rotation of said second chamber.

12. A blood processing system as defined in claim 11 wherein said sidewalls are ech of constant cylindrical radius about the axis of rotation of said carriage whereby the platelets are subjected to a substantially uniform centrifugal force field.

13. A blood processing system as defined in claim 11 wherein said thin interior chamber has a generally rectangular outline when viewed normally from said sidwalls.

14. A blood processing system as defined in claim 11 wherein said second processing chamber is inclined with respect to said axis of rotation so as to have a smaller cylindrical radius at its top than at its bottom.

15. A blood procesing system for centrifugally separating the red blood cell component from whole blood comprising, in combination:
    a processing chamber having first and second closely spaced sidewalls defining an interior chamber having a relatively narrow rounded lower portion, and a relatively wide upper portion including relatively widely spaced shoulder portions;
    inlet means including an inlet port in said chamber for admitting blood to be processed to said chamber;
    outlet means including at least one outlet port in said chamber adjacent at least one of said shoulder portions for deriving the red blood cell component from said chamber; and
    means including a rotatably driven carriage for rotating said chamber, said chamber being aligned thereon in a plane generally inclined from the axis of rotation of said carriage with the cylindrical radius of said upper portion smaller than the cylindrical radius of said lower portion whereby the red blood cell component tends to collect in said shoulder portions.

16. A blood processing system as defined in claim 15 wherein said processing chamber is distensible and formed in collapsed flat condition, and wherein said carriage includes a carrier comprising first and second rigid plates defining therebetween an interior compartment for receiving said processing chamber and removable from said rotor to facilitate loading said chamber therein, whereby when the interior of said chamber is filled with blood to be processed said chamber assumes the predetermined configuration of said interior compartment.

17. A blood processing system as defined in claim 16 wherein said processing chamber is formed from first and second sheets of hemo-compatible plastic with a peripheral seal therebetween.

18. A blood processing system as defined in claim 17 wherein said carrier contains rib or ridge means establishing a pressure seal inwardly of said peripheral seal to relieve the pressure than would otherwise be exerted by the contents of said chamber on said peripheral seal.

19. A blood processing system for centrifugally separating red blood cell and platelet components from whole blood comprising, in combination:
 a first processing chamber having first and second closely spaced sidewalls defining an interior chamber having a relatively narrow rounded lower portion, and a relatively wide upper portion including relatively widely spaced shoulder portions;
 means including at least one outlet port in said chamber adjacent at least one of said shoulder portions, and at least one additional outlet port in said chamber intermediate said shoulder portions, and an inlet port, for establishing a fluid flow path through said first chamber;
 a second processing chamber having first and second closely spaced side walls defining a thin interior chamber therebetween;
 means including an inlet port and an outlet port in said second chamber for establishing a fluid flow path therethrough;
 means for introducing whole blood into said first chamber through said inlet port thereof;
 means for establishing fluid communication between said additional outlet port of said first chamber and said inlet port of said second chamber; and
 means including a rotatably driven carriage for rotating said first and second chambers, said chambers being aligned thereon in respective planes with at least said first processing chamber being inclined from the axis of rotation of said carriage with the cylindrical radius of the upper portion thereof being smaller than the cylindrical radius of said lower portion thereof; and
 means for establishing fluid flow into said first chamber and from said first chamber to said second chamber whereby said red blood cell component tends to collect in said shoulder portions and said platelet component tends to sediment within said second chamber.

20. A blood processing system as defined in claim 19 wherein said first and second processing chambers are distensible and formed in collapsed flat condition, and wherein said carriage includes first and second carriers, each of said carriers comprising first and second rigid plates defining therebetween an interior compartment for receiving a respective one of said processing chambers, whereby when the interiors of said chambers are filled with blood fluid to be processed said chambers assume the predetermined configurations of their respective compartments.

21. A blood processing system as defined in claim 20 herein said compartments are each formed from first and second sheets of hemo-compatible plastic with a peripheral seal therebetween.

22. A blood processing system as defined in claim 21 wherein said carriers each contain rib or ridge means establishing pressure seals inwardly of said peripheral seals to relieve the pressure that would otherwise be exerted by the contents of said chambers on said peripheral seals.

23. In a centrifugal inter-vivos blood processing system of the type having a rotatably driven carriage for separating the red blood cell component from whole blood, a processing chamber having first and second closely spaced side walls defining an interior chamber having a relatively narrow rounded lower portion, and a relatively wide upper portion including relatively widely spaced shoulder portions;
 means including at least one outlet port in said chamber adjacent at least one of said shoulder portions, and at least one additional outlet port in said chamber intermediate said shoulder portions, and an inlet port, for establishing a fluid flow path through said first chamber; and
 means for introducing whole blood to be processed to said inlet port whereby the red blood component tends to collect at said shoulder portions when said chamber is mounted for rotation on said carriage with the plane containing the largest dimensions of said processing chamber generally inclined from a parallel arrangement with respect to the axis of rotation of said carriage, with the upper end thereof at a smaller cylindrical radial distance than the lower end thereof.

24. A processing chamber as defined in claim 23 wherein collection means are provided for deriving blood to be processed from a donor, and injection means are provided for returning processed blood fluid to the donor.

25. A blood processing system as defined in claim 24 wherein said processing chamber is distendable and formed in collapsed flat condition, and wherein said carriage includes a carrier defining an interior compartment for receiving said chamber whereby when the interior of said chamber is filled with blood to be processed said chamber assumes the predetermined configuration of said interior compartment.

26. A blood processing system as defined in claim 25 wherein said processing chamber is formed from first and second sheets of hemo-compatible plastic with a peripheral seal therebetween.

27. A processing chamber as defined in claim 26 wherein collection means are provided for deriving blood to be processed from a donor, and injection means are provided for returning processed blood fluid to the donor.

28. In a centrifugal inter-vivos processing system of the type having a rotatably driven carriage for separating the red blood cell and platelet components from whole blood, a fluid flow system comprising:
 a processing chamber having first and second closely spaced side walls defining an interior chamber having a relatively narrow rounded lower portion, and a relatively wide upper portion including relatively widely spaced shoulder portions;
 means including at least one outlet port in said chamber adjacent at least one of said shoulder portions, and at least one additional outlet port in said chamber intermediate said shoulder portions, and an inlet port, for establishing a fluid flow path through said first chamber;

a second processing chamber having first and second closely spaced side walls defining a thin interior chamber therebetween;

means including an inlet port and an outlet port in said second chamber for establishing a fluid flow path therethrough;

means for estblishing fluid communication between said additional outlet port of said first chamber and said inlet port of said second chamber;

whereby the red blood component tends to collect at shoulder portions within said first chamber and the platelet component tends to sediment in said second chamber when said chambers are mounted for rotation on said carriage in respective planes, with the plane of said first chamber being inclined with repect to a parallel direction with said axis of rotation with the upper end thereof at a smaller cylindrical radial distance than the lower end thereof.

29. An inter-vivos blood processing flow system as defined in claim 28 wherein said processing chambers are distendable and formed in flat collapsed condition.

30. An inter-vivos blood processing flow system as defined in claim 29 wherein said processing chambers are each formed from first and second sheets of hemocompatible plastic with a peripheral seal therebetween.

31. A blood processing system as defined in claim 30 wherein collection means are provided for deriving blood to be processed from a donor, and injection means are provided for returning processed blood fluid to the donor.

* * * * *